(12) United States Patent
Hayashi et al.

(10) Patent No.: US 8,497,985 B2
(45) Date of Patent: Jul. 30, 2013

(54) INSPECTION METHOD BASED ON CAPTURED IMAGE AND INSPECTION DEVICE

(75) Inventors: Yoshinori Hayashi, Yokohama (JP); Hiroshi Wakaba, Yokohama (JP); Yoko Ono, Yokohama (JP); Koichi Miyazono, Yokohama (JP); Masao Kawamura, Yokohama (JP); Hideki Mori, Yokohama (JP)

(73) Assignee: Shibaura Mechatronics Corporation, Yokohama-shi (JP)

( * ) Notice: Subject to any disclaimer, the term of this patent is extended or adjusted under 35 U.S.C. 154(b) by 471 days.

(21) Appl. No.: 12/738,768

(22) PCT Filed: Oct. 22, 2008

(86) PCT No.: PCT/JP2008/069126
§ 371 (c)(1),
(2), (4) Date: Apr. 19, 2010

(87) PCT Pub. No.: WO2009/054404
PCT Pub. Date: Apr. 30, 2009

(65) Prior Publication Data
US 2010/0245810 A1 Sep. 30, 2010

(30) Foreign Application Priority Data

Oct. 23, 2007 (JP) ................................. 2007-275835

(51) Int. Cl.
*G01N 21/00* (2006.01)
*G01J 4/00* (2006.01)

(52) U.S. Cl.
USPC ........................................ 356/237.2; 356/364

(58) Field of Classification Search
USPC ..... 356/237.1–241.6, 242.1–243.8, 426–431, 356/600–640
See application file for complete search history.

(56) References Cited

U.S. PATENT DOCUMENTS

| | | | | |
|---|---|---|---|---|
| 4,028,728 A | * | 6/1977 | Sharp | 348/131 |
| 5,019,898 A | * | 5/1991 | Chao et al. | 348/34 |
| 5,479,252 A | * | 12/1995 | Worster et al. | 356/237.5 |
| 5,963,314 A | * | 10/1999 | Worster et al. | 356/237.2 |
| 5,984,478 A | * | 11/1999 | Doany et al. | 353/84 |
| 6,347,014 B1 | * | 2/2002 | Hayashi et al. | 359/634 |
| 6,950,545 B1 | * | 9/2005 | Nomoto et al. | 382/141 |

* cited by examiner

*Primary Examiner* — Gregory J Toatley
*Assistant Examiner* — Jarreas C Underwood
(74) *Attorney, Agent, or Firm* — Kratz, Quintos & Hanson, LLP

(57) ABSTRACT

A method of inspection and inspection apparatus able to use a captured image to more precisely inspect the state of film, defect parts, etc. at a surface of an object under inspection are provided.

A method of inspection and inspection apparatus illuminating a surface of an object under inspection 10 by white light from an illumination unit $L_O$ while scanning the surface of the object under inspection 10 by an image capturing unit 100 to acquire a captured image and using the captured image to inspect a state of the surface of the object under inspection 10, which changes a state of polarization of light $L_R$ striking the image capturing unit 100 from an illuminated location of the object under inspection 10 and obtains a plurality of captured images based on light of different polarization states LR striking the image capturing unit 100.

6 Claims, 5 Drawing Sheets

INSPECTION METHOD BASED ON CAPTURED IMAGE AND INSPECTION DEVICE

TECHNICAL FIELD

The present invention relates to a method of inspection and inspection apparatus capturing an image of the surface of a semiconductor wafer or other object under inspection and using the captured image as a basis to inspect the object.

BACKGROUND ART

In the past, an inspection apparatus for detecting defects at a circumferential end face of a semiconductor wafer (external inspection apparatus) has been proposed (for example, Patent Literature 1). This inspection apparatus scans the circumferential end face of the semiconductor wafer under inspection by a line sensor and analyzes the image obtained based on the density (gray-scale) signal obtained for each pixel at that time to generate information showing defects, scratches, foreign matter, etc. at the circumferential end face. According to such an inspection apparatus, it is possible to judge a relief state of the circumferential end face of a semiconductor wafer or what kind of defects there are at the circumferential end face.

In this regard, the process of production of a semiconductor wafer includes a step of forming an oxide film, nitride film, polycrystalline silicon film, aluminum film, and other films, a photolithography step of coating, exposing, and developing a photosensitive material (resist) etc., a step of etching to partially remove the resist film formed on the semiconductor wafer in the photolithography step, etc. If it were possible to learn the states of the various types of films formed on the surface of a semiconductor wafer by such steps, it would be possible to judge if the conditions in the film-forming step, photolithography step, and etching step were suitable. For this reason, it has been desired to detect the states of films on the semiconductor wafer surface as well as the scratches and other defects.

Patent Literature 1: Japanese Patent Publication (A) No. 2000-114329

DISCLOSURE OF THE INVENTION

Technical Problem

However, with a captured image obtained by a density signal from a line sensor like in the above-mentioned conventional inspection apparatus, even with different states of scratches or other defects (relief parts) and different types of films, parts appearing with the same extent of density or parts with the same extent of tinge cannot be differentiated. For example, a copper (Cu) coating layer and a certain thickness of $SiO_2$ layer both have a reddish tinge and are difficult to differentiate on a captured image. In such a case, it is difficult to obtain good precision inspection results.

The present invention was made in consideration of this situation and provides a method of inspection and inspection apparatus enabling the state of a film or defect part etc. at the surface of an object under inspection to be more precisely inspected based on a captured image.

Solution to Problem

The inspection method according to the present invention provides a method of inspection illuminating a surface of an object under inspection by white light from an illumination unit while scanning a surface of the object under inspection by an image capturing unit to obtain a captured image and using the captured image as a basis to inspect the state of the surface of the object under inspection, the method having a first step of changing a state of polarization of light striking the image capturing unit from an illuminated location of the object under inspection and a second step of obtaining a plurality of captured images based on light of different polarization states striking the image capturing unit.

Due to such a configuration, a plurality of captured images are obtained based on light of different polarization states, so even if parts with different optical rotation degrees at the surface of the object under inspection are the same in reflection characteristics against white light (color etc.), the method of expression on the plurality of captured images can differ One or more polarization devices having predetermined polarization characteristics (polarization directions) may be inserted or not inserted into the light path or the polarization devices may be rotated etc. to change the polarization state of the light striking the image capturing unit.

Further, the inspection method according to the present invention can be configured so that the first step changes the polarization state of white light from the illumination unit illuminating the surface of the object under inspection.

Due to such a configuration, even without directly changing the polarization state of the light reflected at the surface of the object under inspection and striking the image capturing unit, the polarization state of white light emitted from the illumination unit can be changed, so as a result the polarization state of the light striking the image capturing unit can be changed.

Further, the inspection method according to the present invention can be configured so that the first step changes the polarization state of reflected light after the white light emitted from the illumination unit is reflected at the surface of the object under inspection.

Due to such a configuration, even without the polarization state of the white light emitted from the illumination unit and striking the surface of the object under inspection being changed, the polarization state of light reflected at the object under inspection can be changed, so the polarization state of the light entering the image capturing unit can be changed.

Furthermore, the inspection method according to the present invention can be configured so that a polarization member is set at either of a light path by which the white light emitted from the illumination unit reaches the surface of the object under inspection and a light path by which reflected light from the surface of the object under inspection reaches the image capturing unit, and the first step changes the polarization direction of the polarization member.

Due to such a configuration, by changing the polarization direction of the polarization member, at least one of a polarization state of white light emitted from the illumination unit and reaching the surface of the object under inspection and a polarization state of reflected light at the surface of the object under inspection can be changed, so the polarization state of the light striking the image capturing unit can be changed.

Further, the inspection method according to the present invention can be configured so that the polarization member has a first polarization device provided in a light path by which the white light from the illumination unit reaches the surface of the object under inspection and a second polarization device provided in a light path by which reflected light from the surface of the object under inspection reaches the image capturing unit, and the first step changes a polarization direction of at least one of the first polarization device and the second polarization device.

Due to such a configuration, by changing the polarization direction of at least one of the first polarization device and the second polarization device, the polarization state of the light running along the light path from the illumination unit to the surface of the object under inspection and furthermore from that surface to the image capturing unit can be changed, so the polarization state of the light entering the image capturing unit can be changed.

Further, the inspection apparatus according to the present invention has an illumination unit illuminating a surface of an object under inspection by white light, an image capturing unit capturing an image of the surface of the object under inspection, and a processing unit obtaining the image captured by the image capturing unit and using the captured image as a basis to perform processing relating to inspection of the state of the object under inspection, which inspection apparatus is configured so that the apparatus has a polarization member arranged at least at one of a light path by which white light emitted from the illumination unit reaches the surface of the object under inspection and a light path by which reflected light from the surface of the object under inspection reaches the image capturing unit and so that the processing unit has a means for acquiring a plurality of captured images from the image capturing unit in a state with the polarization member used to change polarization characteristics of light reaching the image capturing unit and can use the relationship between the acquired plurality of captured images and the corresponding polarization characteristics as a basis to judge the state of the surface of the object under inspection.

ADVANTAGEOUS EFFECTS OF INVENTION

According to the inspection method and inspection apparatus according to the present invention, even if parts with different optical rotation degrees at the surface of an object under inspection are the same in reflection characteristics against white light (tinge etc.), the method of expression on the plurality of captured images can differ, so these captured images can be used as a basis to more precisely inspect the state of film, defect parts, etc. at the surface of the object under inspection.

Figure 1:
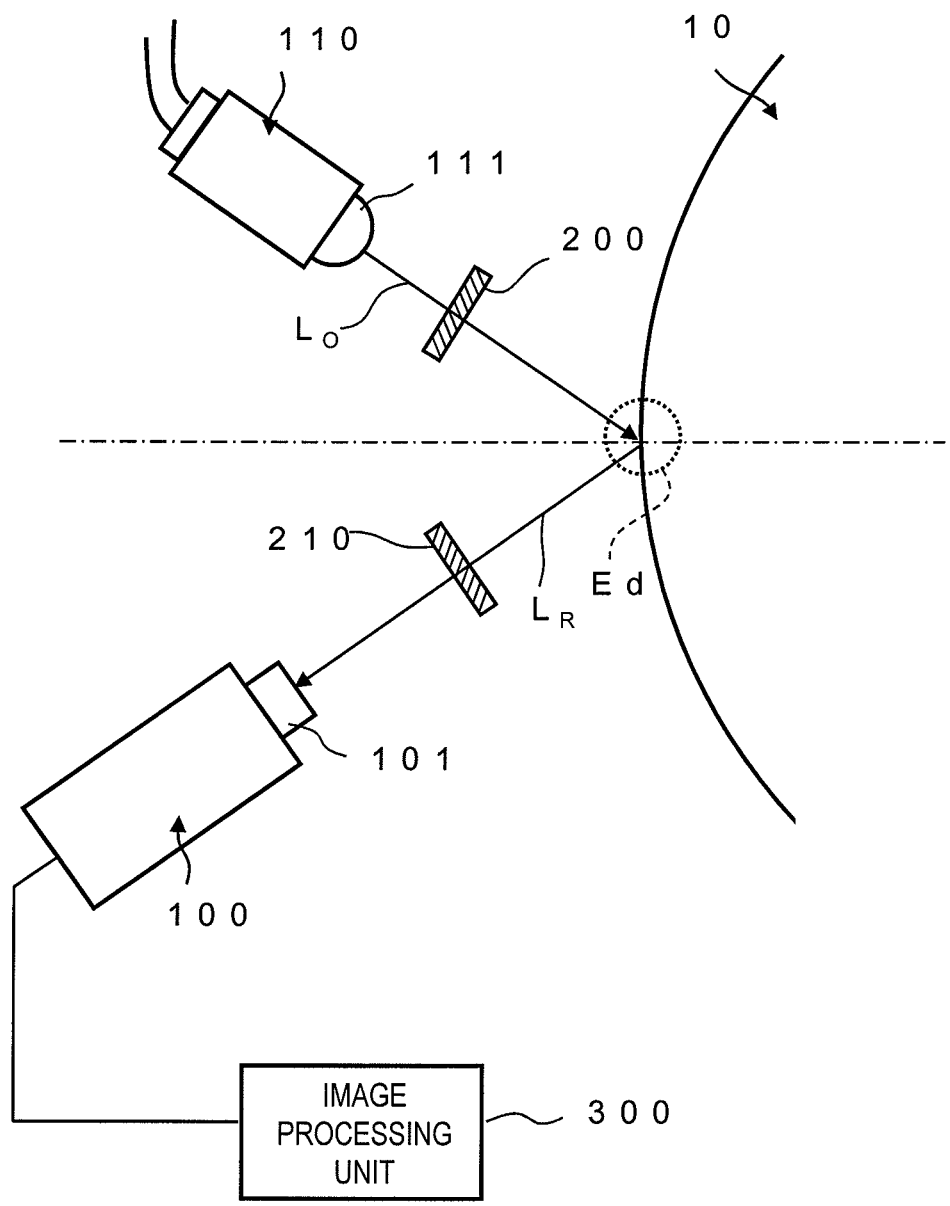
FIG. 1 A view showing a first example of an edge inspection apparatus of a semiconductor wafer (inspection apparatus) performing inspection according to the inspection method according to the present invention.

REFERENCE SIGNS LIST 10 semiconductor wafer (object under inspection)
100 camera unit
101 lens
102 CCD line sensor
110 illumination unit
111 condensing lens
120 half mirror
200 first polarization device
210 second polarization device
300 image processing unit

BEST MODE FOR CARRYING OUT INVENTION

Below, embodiments of the present invention will be explained using the drawings.

The method of inspection according to an embodiment of the present invention is, for example, worked as an edge inspection apparatus of a semiconductor wafer. A first example of this edge inspection apparatus of a semiconductor wafer is configured as shown in FIG. 1.

In FIG. 1, a camera unit 100 (image capturing unit) and illumination unit 110 (illumination unit) are provided so as to face the object under inspection constituted by a semiconductor wafer (below, referred to simply as the "wafer") 10 at the outer circumference end face. The camera unit 100 is arranged with a predetermined angle with respect to the diametrical direction of the wafer 10 (see dot-chain line) so as to approach the image capturing location Ed of the outer circumference end face. Further, the illumination unit 110 is arranged with a predetermined angle with respect to the diametrical direction of the wafer 10 (see dot-chain line) at the opposite side so as to approach the image capturing location Ed of the outer circumference end face.

The wafer 10, while not shown, is set by an alignment mechanism on the stage of a rotation apparatus coaxially and is designed to be rotated along with rotation of the stage. The illumination unit 110 emits white light from an internal white light source. The white light $L_O$ is fired through a condensing lens 111 to an image capturing location Ed of a wafer 10. At the image capturing location Ed of the wafer 10, the white light $L_O$ is reflected. The reflected light $L_R$ strikes the camera unit 100. The camera unit 100 has an imaging device comprised of a CCD line sensor. The CCD line sensor is provided so as to extend in a direction vertical to the surface of the wafer 10 (vertical to the paper surface of FIG. 1) and is designed so that the reflected light $L_R$ from the lens 101 is input to the CCD line sensor. In the light path from the illumination unit 110 to the image capturing location Ed of the outer circumference end face of the wafer 10, a first polarization device 200 is provided, while in the light path from the image capturing location Ed at the outer circumference end face of the wafer 10 to the camera unit 100, a second polarization device 210 is provided.

The image signals successfully output from the camera unit 100 in the process of the wafer 10 rotating are supplied to the image processing unit 300. Due to the image processing unit 300, a captured image extending corresponding to the circumferential direction of the outer circumference end face of the wafer 10 is generated. Further, predetermined inspection processing is performed based on that captured image.

Figure 2A:
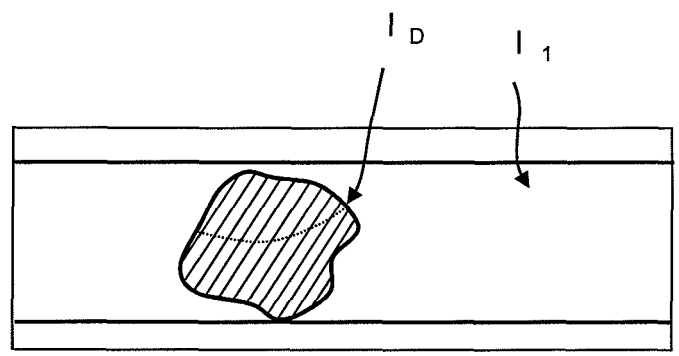
FIG. 2A A view showing an example of a captured image in the case where the polarization directions of the first polarization device and the second polarization device are parallel.

The polarization direction of the first polarization device 200 and the polarization direction of the second polarization device 210 are for example set to be parallel (vertical direction or horizontal direction). In that state, white light $L_O$ is emitted from the illumination unit 110 and the image capturing location Ed of the wafer 10 is captured at the camera unit 100. In this state, the white light $L_O$ from the illumination unit 110 is polarized by the first polarization device 200 and illuminates the image capturing location Ed at the outer circumference end of the wafer 10. Furthermore, the reflected light $L_R$ at the image capturing location Ed of the white light $L_O$ is polarized by the second polarization device 210. The polarized reflected light $L_R$ enters the camera unit 100. The polarization state of the light entering the camera unit 100 is based on the polarization action of the first polarization device 200 and second polarization device 210 with parallel polarization directions, while the image processing unit 300 acquires a captured image based on the light in the state receiving this polarization action. For example, a captured image $I_1$ as shown in FIG. 2A is obtained. This captured image $I_1$ corresponds to the outer circumference end face of the wafer 10. Inside this captured image $I_1$, for example, there is an image part $I_D$ corresponding to film layers and other deposits.

Figure 2B:
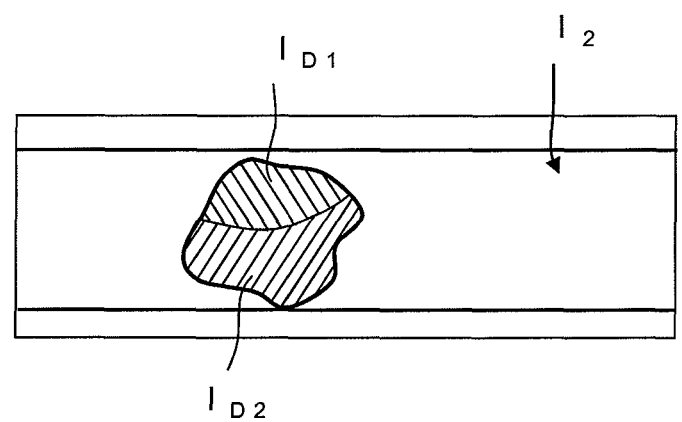
FIG. 2B A view showing an example of a captured image in the case where the polarization directions of the first polarization device and the second polarization device are orthogonal.

Next, the polarization direction of the first polarization device 200 and the polarization direction of the second polarization device are set to be orthogonal. In that state, an image is similarly captured. In this case, as explained above, polarized reflected light $I_R$ enters the camera unit 100. The polarization state of the entering light differs from the one explained above and is based on the polarization action of the first polarization device 200 and second polarization device 210 with orthogonal polarization directions. The image processing unit 300 acquires a captured image based on the light in the state receiving this polarization action, for example, the captured image $I_2$ shown in FIG. 2B. In this captured image $I_2$, for example, the image part $I_D$ at the captured image $I_1$ is differentiated into two part images $I_{D1}$, $I_{D2}$.

The amount of the reflected light $L_R$ from the image capturing location Ed entering the camera unit 100 is affected by the optical rotation degrees of the surface of the wafer 10 or film layers or other deposits in the image capturing location Ed. Therefore, from the differences between the two captured images $I_1$ and $I_2$ (FIG. 2A and FIG. 2B), it is learned that the deposits on the outer circumference end face of the wafer 10 corresponding to the image part $I_D$ of the captured image $I_1$ include at least two parts of different properties corresponding to the image parts $I_{D1}$ and $I_{D2}$ of the captured image $I_2$. Further, the part corresponding to one image part $I_{D1}$ in the deposits can be judged to be the property of having an optical rotation degree changing in manner of expression on the captured image when changing the relationship of the polarization directions of the first polarization device 200 and the second polarization device (orthogonal relationship and parallel relationship). Further, the part corresponding to the other image part $I_{D2}$ in the deposits can be judged to be the property of having an optical rotation degree not changing in manner of expression on the captured image I even when changing the relationship of the polarization directions of the first polarization device 200 and the second polarization device (orthogonal relationship and parallel relationship).

Due to this, the image processing unit 300 is designed to acquire captured images with different polarization characteristics (see FIG. 2A and FIG. 2B) as explained above and to use the relationship (combination) of the methods of expression on a plurality of captured images and polarization characteristics (state) to judge (inspect) the state of the surface of the wafer 10 corresponding to the captured images, for example, deposits etc. Therefore, it becomes possible to use the captured images to more precisely inspect the state of the film or defect parts etc. on the surface of the wafer 10. Note that, the image processing unit 300 may also display the plurality of captured images on a display unit (not shown) so as to enable the correspondence of the plurality of captured images and their polarization characteristics to be understood and leave the judgment of the state of the surface of the wafer 10 to the operator. Further, the image processing unit 300 can use the correspondence between the plurality of captured images and their polarization characteristics to automatically identify the state of the surface of the wafer 10, for example, the position, type, etc. of the deposits etc. and output the results.

Figure 3:
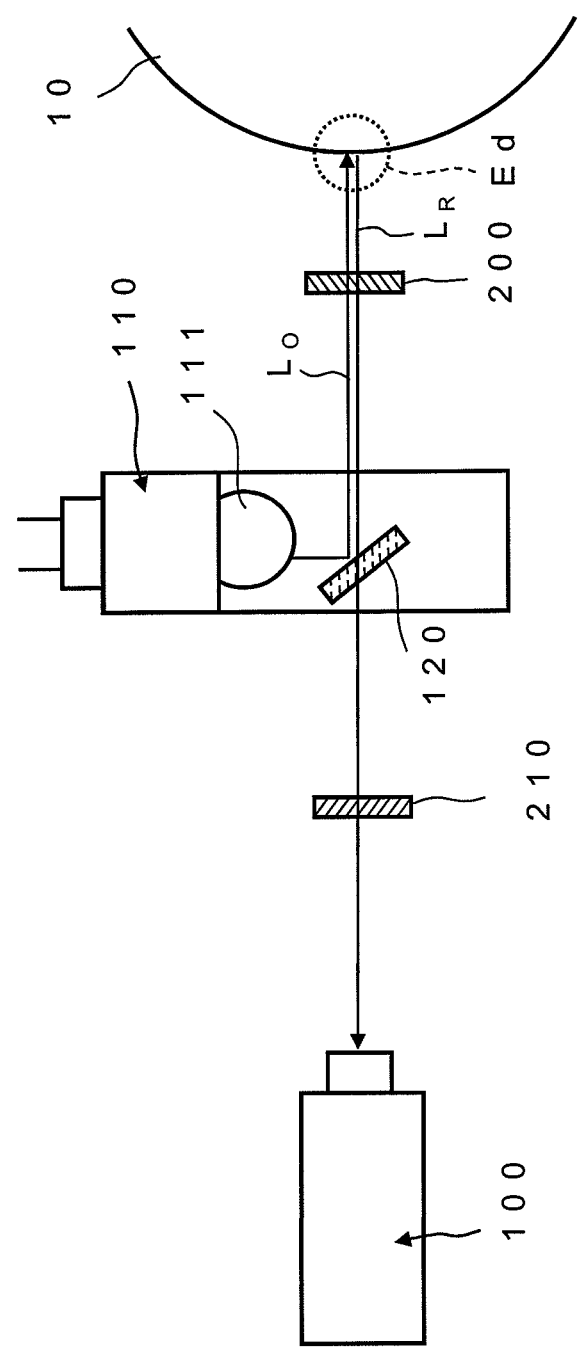
FIG. 3 A view showing a second example of an edge inspection apparatus of a semiconductor wafer (inspection apparatus) performing inspection according to the inspection method according to the present invention.

A second example of the edge inspection apparatus of a semiconductor wafer is shown in FIG. 3. Note that, in FIG. 3, the image processing unit 300 is omitted. In this second example, the optical axis of the white light $L_O$ striking the image capturing location Ed and the optical axis of the reflected light $L_R$ at the image capturing location Ed match, that is, a coaxial configuration is adopted.

In FIG. 3, the camera unit 100 is arranged so that its optical axis matches the diametrical direction of the wafer 10. The first polarization device 200 and the second polarization device 210 are set in the light path from the image capturing location Ed of the outer circumference end face of the wafer 10 to the camera unit 100. Between the first polarization device 200 and the second polarization device 210, a half mirror 120 is set. The white light $L_O$ emitted from the white light source of the illumination unit 110 through the condensing lens 111 is reflected at the half mirror 120 and furthermore polarized through the first polarization device 200. In that state, it strikes the image capturing location Ed of the outer circumference end face of the wafer 10. Further, the reflected light LR at the image capturing location Ed of the outer circumference end face of the wafer 10 is polarized at the first polarization device 200, passes through the half mirror 120, is furthermore polarized at the second polarization device 210, and reaches the camera unit 100.

In this edge inspection apparatus (second example) as well, in the same way as the above-mentioned example, it is possible to use the plurality of captured images obtained from the camera unit 100 in the state changing the polarization direction of the first polarization device 200 and the polarization direction of the second polarization device 210 so as to inspect the state of the surface of the outer circumference end face of the wafer 10.

Figure 4:
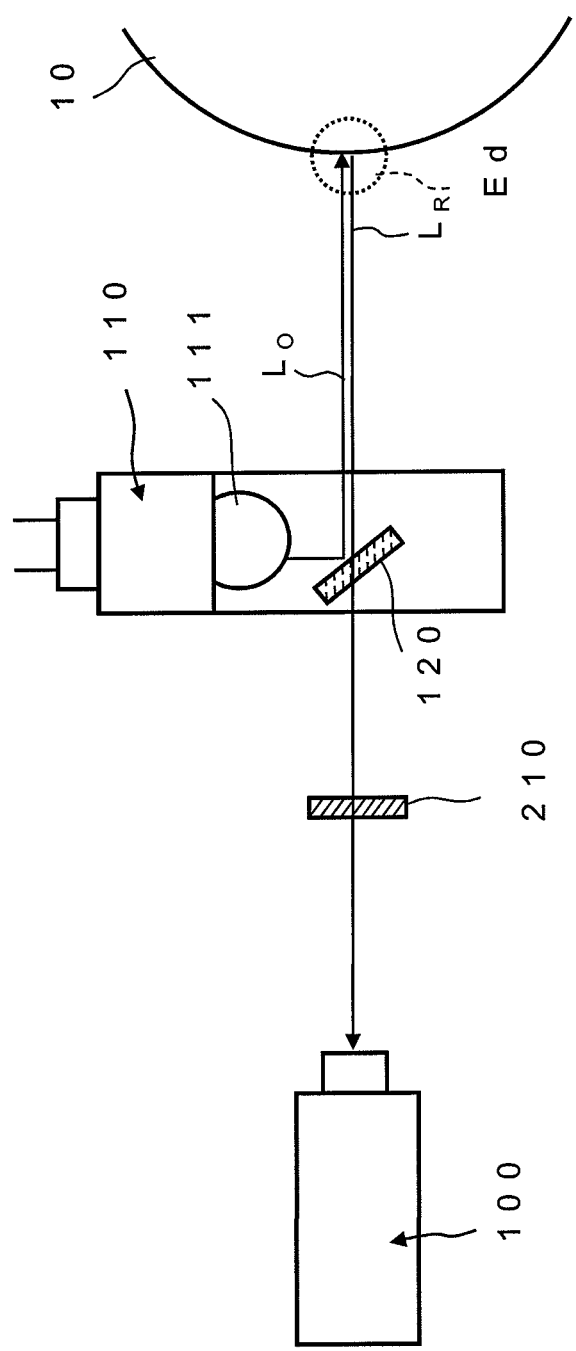
FIG. 4 A view showing a third example of an edge inspection apparatus of a semiconductor wafer (inspection apparatus) performing inspection according to the inspection method according to the present invention.

A third example of the edge inspection apparatus of a semiconductor wafer is shown in FIG. 4. Note that, in FIG. 4, the image processing unit 300 is omitted. This third example is configured with the first polarization device 200 in the second example shown in FIG. 3 removed. In this third example, the white light $L_O$ emitted from the illumination unit 110 is not polarized until reaching the image capturing location Ed of the outer circumference end face of the wafer 10. The reflected light LR at the image capturing location Ed is polarized by the second polarization device 210 and reaches the camera unit 100 in that state. In this case, it is possible to change the polarization direction of the second polarization device 210 (for example, vertical direction and horizontal direction) and use the camera unit 100 to scan the surface of the wafer 10 to obtain a plurality of captured images. It is possible to use the plurality of captured images so as to inspect the state of the surface of the outer circumference end face of the wafer 10.

In each example, the polarization directions of the first polarization device 200 and the second polarization device 210 were changed to obtain a plurality of captured images, but it is also possible to use captured images obtained in the state with at least one of the first polarization device 200 and second polarization device inserted in the light path and in the state with at least one removed to perform the inspection. Furthermore, the method of changing the polarization directions of the polarization devices 200 and 210 need not be changes of 90 degrees in the vertical direction and horizontal direction and may be any angle (20 degrees, 30 degrees, 45 degrees, etc.)

Note that, it is possible to identify a substance used according to the conditions of the production process of the wafer 10 to a certain extent. For this reason, when a material to be discriminated is known, it is possible to confirm in advance the optimum conditions for the polarization state by the optical rotation degree of the material. By obtaining a plurality of captured images in accordance with these conditions and conditions different from these, it is possible to conduct inspections more efficiently.

Figure 5:
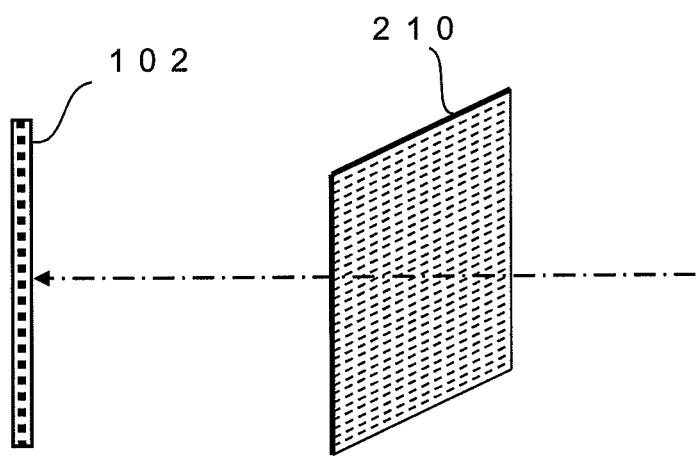
FIG. 5 A view showing an example of the layout of a CCD line sensor and polarization device.

For example, in a camera unit 100 using a CCD line sensor (one-dimensional line sensor) as an imaging capturing element, as shown in FIG. 5, it is possible to obtain captured images in the state where the pixel array direction of the CCD line sensor 102 and the polarization direction of the polarization device 210 perpendicularly cross and the state where the polarization device 210 is removed and use the captured images as the basis for inspection.

Note that, the object under inspection is not limited to the above-mentioned semiconductor wafer. It may also be a DVD or other disk-shaped storage medium or further may be something of a shape other than a disk.

Industrial Applicability

As explained above, the inspection method and inspection apparatus according to the present invention have the advantageous effect of being able to use a captured image as a basis to more precisely inspect the state of film, defect parts, etc. on the surface of an object under inspection and are useful as a method of inspection and inspection apparatus scanning the surface of a semiconductor wafer or other object under inspection and analyzing the captured image to inspect the object under inspection.

The invention claimed is:

1. A method of inspection illuminating a surface of a rotated object under inspection by white light from an illumination unit, scanning a surface of said object under inspection along a rotating direction by an image capturing unit to obtain a captured image, and using said captured image as a basis to inspect the surface of said object under inspection,
    said method having
    a first step of changing a polarization characteristic of light striking the image capturing unit from an illuminated location of said object under inspection and
    a second step of obtaining respective captured images based on light of different polarization characteristics striking said image capturing unit, the light of different polarization characteristics being obtained by changing the polarization characteristic of the light in said first step,
    wherein the surface of said object under inspection is inspected based on a relationship between a plurality of captured images obtained in said second step and the different polarization characteristics of the light striking said image capturing unit when obtaining said plurality of captured images.

2. An inspection method as set forth in claim 1, wherein said first step changes a polarization characteristic of white light from said illumination unit illuminating the surface of the object under inspection.

3. An inspection method as set forth in claim 1, wherein said first step changes the polarization characteristic of reflected light after the white light emitted from said illumination unit is reflected at the surface of the object under inspection.

4. An inspection method as set forth in claim 1, wherein
    a polarization member is set at either of a light path by which the white light emitted from said illumination unit reaches the surface of said object under inspection and a light path by which reflected light from the surface of said object under inspection reaches said image capturing unit, and
    said first step changes the polarization direction of the polarization member.

5. An inspection method as set forth in claim 4, wherein
    said polarization member has a first polarization device provided in a light path by which said white light from the illumination unit reaches the surface of said object under inspection and a second polarization device provided in a light path by which reflected light from the surface of the object under inspection reaches said image capturing unit, and
    said first step changes a polarization direction of at least one of said first polarization device and said second polarization device.

6. An inspection apparatus having:
    a rotating apparatus which rotates an object under inspection,
    an illumination unit illuminating a surface of the rotated object under inspection by white light,
    an image capturing unit capturing an image of the surface of said object under inspection along a rotating direction, and
    a processing unit obtaining the image captured by said image capturing unit and using said captured image as a basis to perform processing relating to inspection of the surface of said object under inspection,
    said inspection apparatus further having
    a polarization member arranged at least at one of a light path by which white light emitted from said illumination unit reaches the surface of said object under inspection and a light path by which reflected light from the surface of said object under inspection reaches said image capturing unit,
    wherein said processing unit has a means for acquiring respective captured images based on light of different polarization characteristics striking said image capturing unit, the light of the different characteristics being obtained by changing the polarization characteristic of the light reaching said image capturing unit by said polarization member, and
    wherein said object under inspection is inspected based on a relationship between a plurality of captured images acquired and the different polarization characteristics of the light striking said image capturing unit when acquiring said plurality of captured images.

* * * * *